United States Patent
Kukreja et al.

(10) Patent No.: US 11,105,784 B2
(45) Date of Patent: Aug. 31, 2021

(54) SYSTEM AND METHOD OF SENSING FOR PETROLEUM, OIL, AND GAS LEAKS USING OPTICAL DETECTION

(71) Applicant: Sensors Unlimited, Inc., Princeton, NJ (US)

(72) Inventors: Sunil L. Kukreja, Avon, CT (US); Joseph V. Mantese, Ellington, CT (US); John Liobe, New York, NY (US)

(73) Assignee: Sensors Unlimited, Inc., Princeton, NJ (US)

( * ) Notice: Subject to any disclaimer, the term of this patent is extended or adjusted under 35 U.S.C. 154(b) by 40 days.

(21) Appl. No.: 16/593,808

(22) Filed: Oct. 4, 2019

(65) Prior Publication Data
US 2021/0102931 A1 Apr. 8, 2021

(51) Int. Cl.
*G01N 21/25* (2006.01)
*G01N 33/22* (2006.01)
*G01N 21/27* (2006.01)

(52) U.S. Cl.
CPC .......... *G01N 33/225* (2013.01); *G01N 21/255* (2013.01); *G01N 21/27* (2013.01); *G01N 2201/06113* (2013.01); *G01N 2201/10* (2013.01)

(58) Field of Classification Search
CPC .................. G01N 21/255; G01N 21/27; G01N 2201/06113; G01N 2201/10; G01N 33/225
See application file for complete search history.

(56) References Cited

U.S. PATENT DOCUMENTS

| | | |
|---|---|---|
| 6,822,742 B1 | 11/2004 | Kalayeh et al. |
| 8,345,250 B1 | 1/2013 | Janosky et al. |
| 10,107,751 B2 | 10/2018 | Scherer et al. |
| 2014/0002667 A1 | 1/2014 | Cheben et al. |
| 2018/0188163 A1 | 7/2018 | Kester et al. |
| 2018/0209902 A1 | 7/2018 | Myshak et al. |
| 2018/0266944 A1 | 9/2018 | Waxman et al. |

OTHER PUBLICATIONS

Castillo Paulo et al: "Open-path quantum cascade laser-based system for simultaneous remote sensing of methane, nitrous oxide, and water vapor using chirped-pulse differential optical absorption spectroscopy", Proceedings of SPIE/IS & T, IEEE, vol. 9640, Oct. 16, 2015, pp. 96400P-96400P.
Zhenhui Du et al: "Mid-Infrared Tunable Laser-Based Broadband Fingerprint Absorption Spectroscopy for Trace Gas Sensing: A Review", Applied Sciences, vol. 9, No. 2, Jan. 18, 2019, p. 338.

(Continued)

*Primary Examiner* — Mark R Gaworecki
(74) *Attorney, Agent, or Firm* — Locke Lord LLP; Scott D. Wofsy; Georgi Korobanov

(57) ABSTRACT

A system for remote detection of fluid leaks from a natural gas or oil pipeline including a laser light source for detecting a methane leak while sweeping in multiple directions, a Midwave Infrared (MWIR) detector optically coupled with the laser light source and a controller operatively connected to the laser light source and the MWIR detector for aggregating data collected by the laser light source and the MWIR using a nuropmophic flow detection algorithm including computational fluid dynamic models.

5 Claims, 2 Drawing Sheets

100

(56) References Cited

OTHER PUBLICATIONS

Thomas A Fox et al: "A review of close-range and screening technologies for mitigating fugitive methane emissions in upstream oil and gas", Environmental Research Letters, BR, vol. 14, No. 5, Apr. 26, 2019, p. 53002.
Wainner Richard T et al: "Scanning, standoff TDLAS leak imaging and quantification", Proceedings of SPIE, vol. 10210, May 5, 2017, pp. 1021006-1021006.
Eric J. Zhang et al: "Field Deployment of a Portable Optical Spectrometer for Methane Fugitive Emissions Monitoring on Oil and Gas Well Pads", Sensors, vol. 19, No. 12, Jun. 16, 2019, p. 2707.
Sean Coburn et al: "Continuous regional trace gas source attribution using a field-deployed dual frequency comb spectrometer", arxiv. org, Cornell University Library, 201 Olin Library Cornell University Ithaca, NY 14853, Nov. 21, 2017, pp. 7-9.
Extended European Search Report dated Jul. 7, 2020, issued during the prosecution of European Patent Application No. EP 19215828.5.

SYSTEM AND METHOD OF SENSING FOR PETROLEUM, OIL, AND GAS LEAKS USING OPTICAL DETECTION

TECHNOLOGICAL FIELD

The present disclosure relates to generally to the field of spectroscopic analysis, specifically, to a spectroscopic analysis of trace gases emanating from natural gas and oil pipelines using laser differential absorption.

DESCRIPTION OF RELATED ART

Natural gas, characteristically, contains a mixture of methane, ethane, and small amounts of other gases. Gas generated by the decomposition of organic matter, henceforth, referred to as swamp gas, only contains methane. It is highly desirable for any natural gas detection method to be able to distinguish between gases released as a result of a failure in a pipeline or a holding container versus emanating swamp gases, thus avoiding false alarms.

Oil pipelines contain significant concentrations of volatile dissolved gas compounds, including methane, ethane, and propane. Oil pipelines operate under pressure; leaks and a concomitant pressure drop result in escaping volatile components, and thereby provide a means for leak detection. Electromagnetic radiation can be directed onto a test subject by any of a variety of means. Commonly, lasers are used but other means such as the use of antennas for radio and microwave electromagnetic energy may be used.

A variety of devices are known in the video based methane gas leak detection using infrared camera technology. Both point and line of sight based sensing, typically fail to detect up to 60% of the significant leaks in a petroleum-oil-gas installation. Operator based video leak detection (VLD) is only capable of volumetric sensing—dividing a particular scene into separate "voxels" that allows leak pinpointing and semi-quantification.

The conventional methods and systems have generally been considered satisfactory for their intended purpose. However, there is still a need in the art for detection systems and methods having improved reliability and accuracy. There also remains a need in the art for such systems and methods that are economically viable. The present disclosure may provide a solution for at least one of these remaining challenges.

SUMMARY OF THE INVENTION

A system for remote detection of fluid leaks from a natural gas or oil pipeline includes laser light source for detecting a methane leak while sweeping in multiple directions a Midwave Infrared (MWIR) detector optically coupled with the laser light source, and a controller operatively connected to the laser light source and the MWIR detector for aggregating data collected by the laser light source and the MWIR using a nuropmophic flow detection algorithm including computational fluid dynamic models. The laser light source can be tuned to absorption peaks between 3.2-3.3 μm. A scanning mechanism can be operatively connected to the laser light source configured to sweep the laser light source from 0 to 80 degrees in a first direction and to sweep the laser light source from 0 to 50 degrees in a second direction orthogonal to the first direction. The MWIR detector can be coupled to a resonant scan mirror configured to generate video data at 60 Hz. The MWIR detector and the laser light source can both be coupled to an aircraft or to a stationary platform.

A method for remote quantitative detection of fluid leaks from a natural gas or oil pipeline is also conceived. The method includes scanning an area including the natural gas or oil pipeline using a laser light source tuned to a methane absorption peak in order to detect a methane leak, scanning the area scanned by the laser light source using an MWIR detector in order to detect a methane leak, imaging on an imaging interface the methane leak using an algorithm including: video analytics of the laser source scan and the MWIR detector scan, methane dispersion modeling using laser scan and the MWIR scan in order to localize fluid leaks, quantifying the methane leak using the algorithm including: video analytics of the laser source scan and the MWIR detector scan, methane dispersion modeling using the laser scan and the MWIR scan in order to localize fluid leaks and quantify methane mass flow rate and communicating an alert if a fluid leak above a predetermined threshold is detected.

The method allows the leaks to localized to within 1 meter and the mass flow rate is quantified to within 10 grams per minute. The methane imaging algorithm and the methane quantifying algorithm comprise differential imaging using two different wavelengths and include using a first model to capture an appearances of methane jets and a second model to capture an appearance of diffuse clouds. The method further includes estimating methane concentration using visual tomography comprising camera pose estimation.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION

Figure 1:
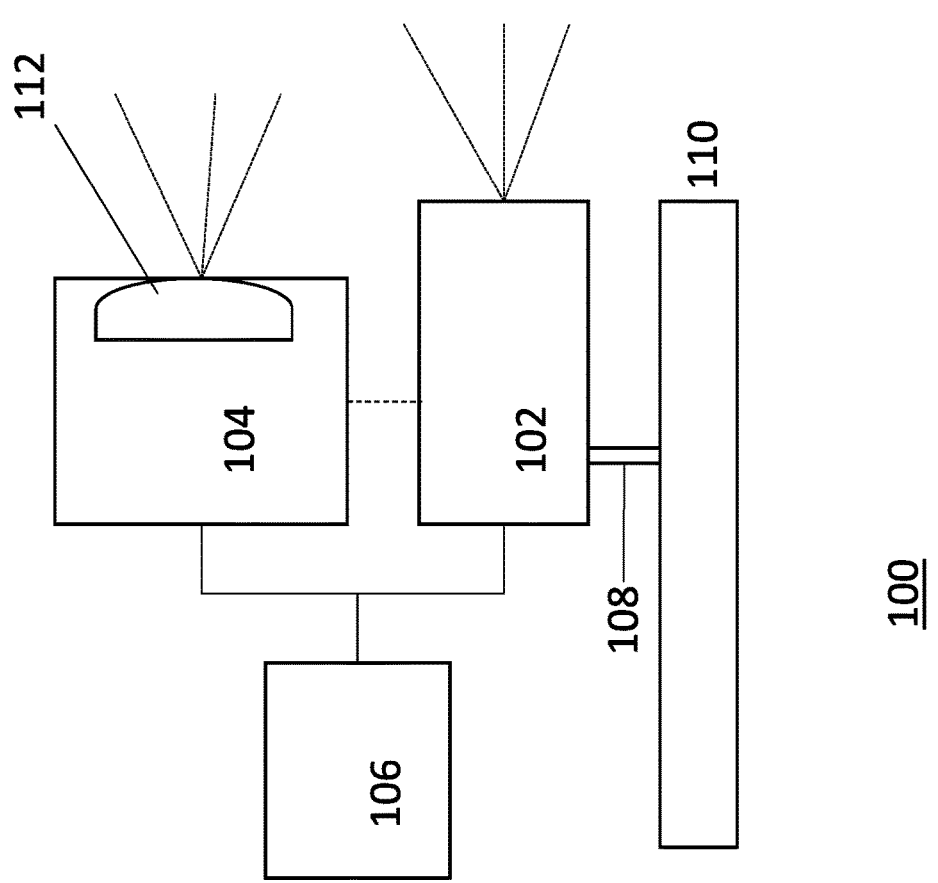
FIG. 1 is a schematic block diagram of an optical detection system.

Reference will now be made to the drawings wherein like reference numerals identify similar structural features or aspects of the subject invention. For purposes of explanation and illustration, and not limitation, a partial view of an exemplary embodiment of a system of optical detection in accordance with the invention is shown in FIG. 1 and is designated generally by reference character 100. The methods and systems of the invention can be used to detect and pinpoint a leak from a pipeline.

FIG. 1 shows, a system 100 for remote detection of fluid leaks from a natural gas or oil pipeline comprising a laser light source 102 for detecting a methane leak while sweeping in multiple directions, a Midwave Infrared (MWIR) detector 104 optically coupled with the laser light source 102 and a controller 106 operatively connected to the laser light source 102 and the MWIR detector 104 for aggregating data collected by the laser light source 102 and the MWIR 104 using a neuropmophic flow detection algorithm including computational fluid dynamic models. The laser light source can be tuned to absorption peaks between 3.2-3.3 µm in order to detect methane. A scanning mechanism 108 is operatively connected to the laser light source 102 in order to allow the laser light source to sweep 80 degrees in a first direction, such as height or vertically, and 50 degrees in a second direction orthogonal to the first direction, such as width or horizontally. The laser light source 102 can be coupled to a platform 110 on an aircraft or to a stationary platform.

The MWIR detector 104 is coupled to a resonant scan mirror 112 configured to generate video data at 640×512 pixels at 60 Hz. The MWIR detector 104 can also be coupled to an aircraft or to a stationary platform affixed to the pipeline.

Figure 2:
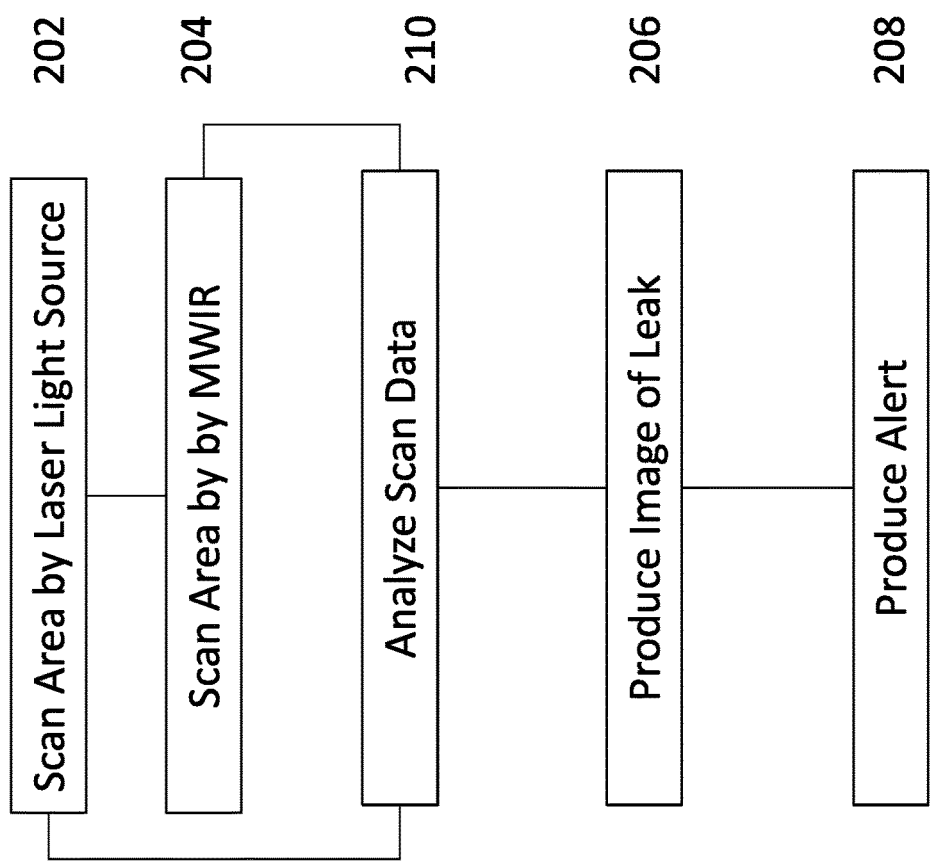
FIG. 2 is a schematic block diagram of a method of use of the optical detection system in FIG. 1.

FIG. 2 shows a schematic of a method 200 for remote quantitative detection of fluid leaks from a natural gas or oil pipeline for the system described above. The method 200 includes scanning an area 202 including the natural gas or oil pipeline using a laser light source tuned to a methane absorption peak in order to detect a methane leak, scanning the area 204 scanned by the laser light source using an MWIR detector in order to detect a methane leak, producing 206 an image on an imaging interface of the methane leak using an algorithm 210. The algorithm 210 includes video analytics of the laser source scan 202 and the MWIR detector scan 204, methane dispersion modeling using laser scan 202 and the MWIR scan 204 in order to localize fluid leaks, quantifying the methane leak using the algorithm including 210. An alert 208 can then be communicated to a user if a fluid leak above a predetermined threshold is detected. The alert 208 can include coordinates and flow rate of the leak. The method 200 allows the leaks to localized to within 1 meter and mass flow rate to be quantified to within 10 grams per minute.

The methane imaging algorithm and quantifying algorithm 210 includes differential imaging using two different wavelengths between about 3.2 and 3.3 µm. The algorithm 210 includes using a first model to capture an appearances of methane jets and a second model to capture an appearance of diffuse clouds. An estimate of methane concentration using visual tomography comprising camera pose estimation can be produced be produced using this method 200.

The methods and systems of the present disclosure, as described above and shown in the drawings, provide for a methane detection system with superior properties including increased reliability and accuracy. While the apparatus and methods of the subject disclosure have been showing and described with reference to embodiments, those skilled in the art will readily appreciate that changes and/or modifications may be made thereto without departing from the spirit and score of the subject disclosure.

What is claimed is:

1. A method for remote quantitative detection of fluid leaks from a natural gas or oil pipeline comprising:
   scanning an area including the natural gas or oil pipeline using a laser light source tuned to a methane absorption peak in order to detect a methane leak;
   scanning the area scanned by the laser light source using an MWIR detector in order to detect a methane leak;
   imaging on an imaging interface the methane leak using an algorithm including:
      video analytics of the laser source scan and the MWIR detector scan, methane dispersion modeling using laser scan and the MWIR scan in order to localize fluid leaks;
      quantifying the methane leak using the algorithm including: video analytics of the laser source scan and the MWIR detector scan, methane dispersion modeling using the laser scan and the MWIR scan in order to localize fluid leaks and quantify methane mass flow rate; and
   communicating an alert if a fluid leak above a predetermined threshold is detected, wherein the methane imaging algorithm and the methane quantifying algorithm include using a first model to capture an appearances of methane jets and a second model to capture an appearance of diffuse clouds.

2. The method of claim 1, wherein the leaks are localized to within 1 meter.

3. The method of claim 1, wherein the mass flow rate is quantified to within 10 grams per minute.

4. The method of claim 1, wherein the methane imaging algorithm and the methane quantifying algorithm comprise differential imaging using two different wavelengths.

5. A method for remote quantitative detection of fluid leaks from a natural gas or oil pipeline comprising:
   scanning an area including the natural gas or oil pipeline using a laser light source tuned to a methane absorption peak in order to detect a methane leak;
   scanning the area scanned by the laser light source using an MWIR detector in order to detect a methane leak;
   imaging on an imaging interface the methane leak using an algorithm including:
      video analytics of the laser source scan and the MWIR detector scan, methane dispersion modeling using laser scan and the MWIR scan in order to localize fluid leaks;
      quantifying the methane leak using the algorithm including: video analytics of the laser source scan and the MWIR detector scan, methane dispersion modeling using the laser scan and the MWIR scan in order to localize fluid leaks and quantify methane mass flow rate;
   communicating an alert if a fluid leak above a predetermined threshold is detected; and
   estimating methane concentration using visual tomography comprising camera pose estimation.

* * * * *